(12) United States Patent
Greenberg et al.

(10) Patent No.: US 9,186,496 B2
(45) Date of Patent: *Nov. 17, 2015

(54) RETINAL PROSTHESIS

(71) Applicant: Second Sight Medical Products, Inc., San Fernando, CA (US)

(72) Inventors: Robert J Greenberg, Los Angeles, CA (US); Neil Hamilton Talbot, La Crescenta, CA (US); Brian V Mech, Santa Clarita, CA (US); James Singleton Little, Newhall, CA (US)

(73) Assignee: Second Sight Medical Products, Inc., Sylmar, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/733,819

(22) Filed: Jan. 3, 2013

(65) Prior Publication Data

US 2013/0144360 A1 Jun. 6, 2013

Related U.S. Application Data

(62) Division of application No. 11/880,009, filed on Jul. 19, 2007, now Pat. No. 7,894,909, and a division of application No. 10/918,112, filed on Aug. 13, 2004, now Pat. No. 7,263,403.

(60) Provisional application No. 60/574,130, filed on May 25, 2004.

(51) Int. Cl.
*A61N 1/18* (2006.01)
*A61N 1/05* (2006.01)
*A61N 1/36* (2006.01)

(52) U.S. Cl.
CPC .......... *A61N 1/0543* (2013.01); *A61N 1/36046* (2013.01)

(58) Field of Classification Search
CPC ............................. A61N 1/36046; A61N 1/05
USPC .............................................. 607/54, 53, 116
See application file for complete search history.

(56) References Cited

U.S. PATENT DOCUMENTS

| 4,573,481 | A | 3/1986 | Bullara |
| 4,628,933 | A | 12/1986 | Michelson |
| 4,837,049 | A | 6/1989 | Byers et al. |
| 5,109,844 | A | 5/1992 | De Juan, Jr. et al. |
| 5,215,088 | A | 6/1993 | Normann et al. |
| 5,935,155 | A | 8/1999 | Humayan et al. |
| 6,393,327 | B1 * | 5/2002 | Scribner .......................... 607/54 |
| 6,400,989 | B1 | 6/2002 | Eckmiller |

(Continued)

OTHER PUBLICATIONS

C. M. Zierhofer and E. S. Hochmair. Coil design for improved power transfer efficiency in inductive links. Int. Conf. Engineering in Medicine and Biology. vol. 4 (1997):pp. 1538-1539.*

*Primary Examiner* — Christopher D Koharski
*Assistant Examiner* — Jeremiah Kimball
(74) *Attorney, Agent, or Firm* — Scott B. Dunbar

(57) ABSTRACT

The invention is a retinal prosthesis with an improved configuration mounting necessary components within and surrounding the eye. The present invention better allows for the implantation of electronics within the delicate eye structure. The invention provides for less height of the part external to the eye by mounting a receiver coil around an electronics package.

8 Claims, 6 Drawing Sheets

(56) References Cited

U.S. PATENT DOCUMENTS

| | | |
|---|---|---|
| 6,458,157 B1 | 10/2002 | Suaning |
| 6,647,297 B2 | 11/2003 | Scribner |
| 6,976,998 B2 * | 12/2005 | Rizzo et al. .................. 623/6.63 |
| 2002/0038134 A1 | 3/2002 | Greenberg et al. |
| 2002/0095193 A1 * | 7/2002 | Ok et al. ........................ 607/54 |
| 2002/0120296 A1 | 8/2002 | Mech et al. |
| 2002/0139556 A1 | 10/2002 | Ok et al. |
| 2003/0149458 A1 | 8/2003 | Williamson et al. |

* cited by examiner

RETINAL PROSTHESIS

CROSS REFERENCE TO RELATED APPLICATIONS

This application is a divisional application of U.S. patent application Ser. No. 13/004,538 (now U.S. Pat. No. 8,369, 957), filed Jan. 11, 2001, which is a divisional application of U.S. patent application Ser. No. 11/880,009 (now U.S. Pat. No. 7,894,909), filed Jul. 19, 2007, which is a divisional application of U.S. patent application Ser. No. 10/918,112 (now U.S. Pat. No. 7,263,403), filed Aug. 13, 2004, which claims priority of provisional Patent Application No. 60/574, 130 filed May 25, 2004, the disclosure of which are both incorporated herein by reference.

GOVERNMENT RIGHTS NOTICE

This invention was made with government support under grant No. R24EY12893-01, awarded by the National Institutes of Health. The government has certain rights in the invention.

FIELD OF THE INVENTION

The present invention is generally directed to a visual prosthesis and more specifically to an improved mechanical and electrical configurations for retinal prosthesis for artificial vision.

BACKGROUND OF THE INVENTION

In 1755 LeRoy passed the discharge of a Leyden jar through the orbit of a man who was blind from cataract and the patient saw "flames passing rapidly downwards." Ever since, there has been a fascination with electrically elicited visual perception. The general concept of electrical stimulation of retinal cells to produce these flashes of light or phosphenes has been known for quite some time. Based on these general principles, some early attempts at devising a prosthesis for aiding the visually impaired have included attaching electrodes to the head or eyelids of patients. While some of these early attempts met with some limited success, these early prosthetic devices were large, bulky and could not produce adequate simulated vision to truly aid the visually impaired.

In the early 1930's, Foerster investigated the effect of electrically stimulating the exposed occipital pole of one cerebral hemisphere. He found that, when a point at the extreme occipital pole was stimulated, the patient perceived a small spot of light directly in front and motionless (a phosphene). Subsequently, Brindley and Lewin (1968) thoroughly studied electrical stimulation of the human occipital (visual) cortex. By varying the stimulation parameters, these investigators described in detail the location of the phosphenes produced relative to the specific region of the occipital cortex stimulated. These experiments demonstrated: (1) the consistent shape and position of phosphenes; (2) that increased stimulation pulse duration made phosphenes brighter; and (3) that there was no detectable interaction between neighboring electrodes which were as close as 2.4 mm apart.

As intraocular surgical techniques have advanced, it has become possible to apply stimulation on small groups and even on individual retinal cells to generate focused phosphenes through devices implanted within the eye itself. This has sparked renewed interest in developing methods and apparati to aid the visually impaired. Specifically, great effort has been expended in the area of intraocular retinal prosthesis devices in an effort to restore vision in cases where blindness is caused by photoreceptor degenerative retinal diseases such as retinitis pigmentosa and age related macular degeneration which affect millions of people worldwide.

Neural tissue can be artificially stimulated and activated by prosthetic devices that pass pulses of electrical current through electrodes on such a device. The passage of current causes changes in electrical potentials across visual neuronal membranes, which can initiate visual neuron action potentials, which are the means of information transfer in the nervous system.

Based on this mechanism, it is possible to input information into the nervous system by coding the information as a sequence of electrical pulses which are relayed to the nervous system via the prosthetic device. In this way, it is possible to provide artificial sensations including vision.

One typical application of neural tissue stimulation is in the rehabilitation of the blind. Some forms of blindness involve selective loss of the light sensitive transducers of the retina. Other retinal neurons remain viable, however, and may be activated in the manner described above by placement of a prosthetic electrode device on the inner (toward the vitreous) retinal surface (epiretinal). This placement must be mechanically stable, minimize the distance between the device electrodes and the visual neurons, and avoid undue compression of the visual neurons.

In 1986, Bullara (U.S. Pat. No. 4,573,481) patented an electrode assembly for surgical implantation on a nerve. The matrix was silicone with embedded iridium electrodes. The assembly fit around a nerve to stimulate it.

Dawson and Radtke stimulated cat's retina by direct electrical stimulation of the retinal ganglion cell layer. These experimenters placed nine and then fourteen electrodes upon the inner retinal layer (i.e., primarily the ganglion cell layer) of two cats. Their experiments suggested that electrical stimulation of the retina with 30 to 100 uA current resulted in visual cortical responses. These experiments were carried out with needle-shaped electrodes that penetrated the surface of the retina (see also U.S. Pat. No. 4,628,933 to Michelson).

The Michelson '933 apparatus includes an array of photosensitive devices on its surface that are connected to a plurality of electrodes positioned on the opposite surface of the device to stimulate the retina. These electrodes are disposed to form an array similar to a "bed of nails" having conductors which impinge directly on the retina to stimulate the retinal cells. U.S. Pat. No. 4,837,049 to Byers describes spike electrodes for neural stimulation. Each spike electrode pierces neural tissue for better electrical contact. U.S. Pat. No. 5,215, 088 to Norman describes an array of spike electrodes for cortical stimulation. Each spike pierces cortical tissue for better electrical contact.

The art of implanting an intraocular prosthetic device to electrically stimulate the retina was advanced with the introduction of retinal tacks in retinal surgery. De Juan, et al. at Duke University Eye Center inserted retinal tacks into retinas in an effort to reattach retinas that had detached from the underlying choroid, which is the source of blood supply for the outer retina and thus the photoreceptors. See, e.g., E. de Juan, et al., 99 Am. J. Ophthalmol. 272 (1985). These retinal tacks have proved to be biocompatible and remain embedded in the retina, and choroid/sclera, effectively pinning the retina against the choroid and the posterior aspects of the globe. Humayun, U.S. Pat. No. 5,935,155 describes the use of retinal tacks to attach a retinal array to the retina. Alternatively, an electrode array may be attached by magnets or glue. U.S. Pat.

No. 5,109,844 to de Juan describes a flat electrode array placed against the retina for visual stimulation.

Any device for stimulating percepts in the retina must receive a signal describing a visual image along with power to operate the device. The device can not be powered by wires as any connection through the skin will create the risk of infection. Battery power is not practical as batteries are bulky and surgery is required to replace them. Such signal and power may be transmitted into the eye inductively as shown in Humayun U.S. Pat. No. 5,935,155. Humayun uses a primary (external) coil in front of the eye, possibly encased within the rim of a pair of glasses, and a secondary (internal) coil within the lens capsule or around the sclera just under the conjunctiva. Implanting within the lens capsule is difficult surgery and only allows for a small diameter coil. Larger coils are more efficient, can receive more power with less resulting temperature rise per unit of power received. Implanting around the sclera under the conjunctiva and near the surgical limbus (that is at the front of the eye) allows for a larger coil but may cause irritation or damage to the conjunctiva if the coil is placed in front near the cornea.

U.S. patent application Ser. No. 09/761,270, Ok, discloses several coil configurations including a configuration where the coil is offset about 45 degrees from the front of the eye. The offset configuration allows the primary and secondary coils to be placed closer together allowing for better inductive coupling. The bridge of nose partially blocks placement of a primary coil when placed directly in front of the eye.

Vision simulations show that approximately 1000 pixels are needed to achieve basic visual functions such a face recognition and reading. It would be difficult or impossible to mount the electronics need for 1000 pixels within the eye. Even if the electronics could be fit within the eye, heat dissipation would be a major issue. It would be equally difficult to pass a cable capable of caring 1000 signal wires through the sclera. New mechanical and electrical configurations are needed to supply such a high density electrode array.

SUMMARY OF THE INVENTION

The invention is a retinal prosthesis with an improved configuration mounting necessary components within and surrounding the eye. The present invention better allows for the implantation of electronics, capable of high resolution display, within the delicate eye structure. The invention further limits the necessary width of a thin film conductor passing through the sclera by use of a multiplexer external to the sclera and a demultiplexer internal to the sclera.

DETAILED DESCRIPTION OF THE PREFERRED EMBODIMENTS

The following description is of the best mode presently contemplated for carrying out the invention. This description is not to be taken in a limiting sense, but is made merely for the purpose of describing the general principles of the invention. The scope of the invention should be determined with reference to the claims.

Figure 1:
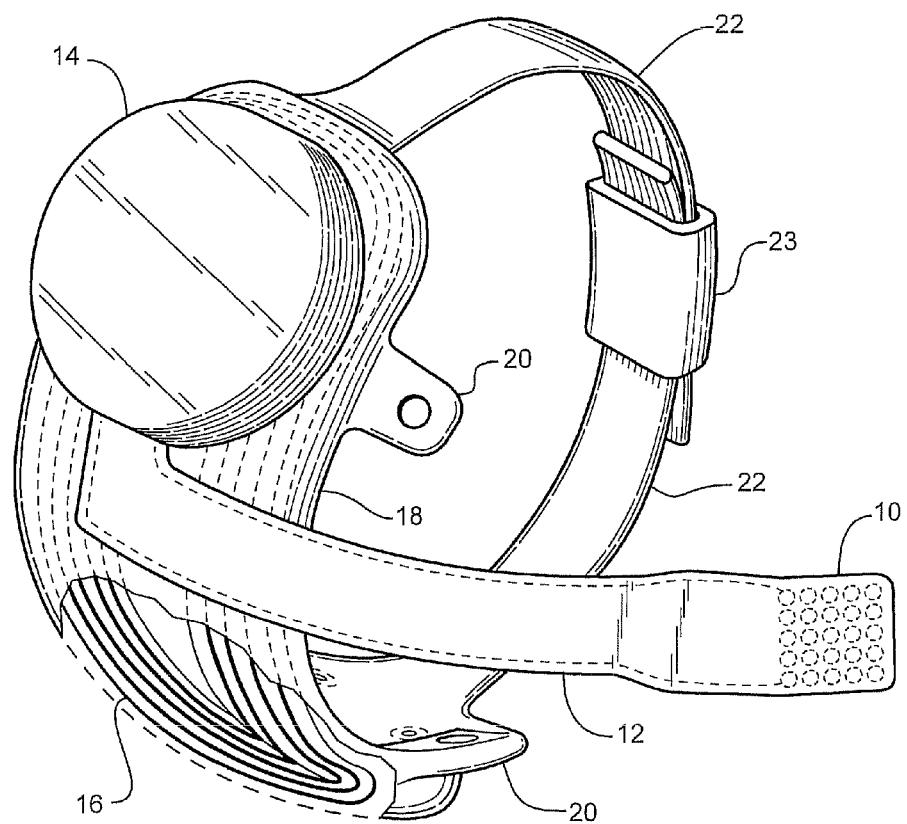
FIG. 1 is a perspective view of the implanted portion of the preferred retinal prosthesis.

FIG. 1 shows a perspective view of the implanted portion of the preferred retinal prosthesis. An electrode array 10 is mounted by a retinal tack or similar means to the epiretinal surface. The electrode array 10 is electrically coupled by a cable 12 which pierces the sclera and is electrically coupled to an electronics package 14, external to the sclera. It is advantageous to encase the electronics within a hermetic package. This can be accomplished by use of a metal, ceramic polymer or a combination of these materials case, or by applying a thin film hermetic coating such as described in US patent application 20020038134 Package for an Implantable Medical Device and 20020120296, Implantable Device Using Ultra-Nanocrystalline Diamond. An electronics package with a coil mounted on the lateral surface of the retina is described in U.S. patent application Ser. No. 10/820,240. All of the above applications are incorporated herein by reference.

It is advantageous to mount electronics external to the sclera, as the fatty tissue there is less heat sensitive, and blood flow rapidly dissipates excess heat. The vitreous within the eye is does not change often and the retina is very heat sensitive.

The electronics package 14 is electrically coupled to a secondary inductive coil 16. Preferably the secondary inductive coil 16 is made from wound wire. Alternatively, the secondary inductive coil may be made from a thin film polymer sandwich with wire traces deposited between layers of thin film polymer. The electronics package 14 and secondary inductive coil 16 are held together by a molded body 18. The molded body 18 may also include suture tabs 20. The molded body narrows to form a strap 22 which surrounds the sclera and holds the molded body 18, secondary inductive coil 16, and electronics package 14 in place. The molded body 18, suture tabs 20 and strap 22 are preferably an integrated unit made of silicone elastomer. Silicone elastomer can be formed in a pre-curved shape to match the curvature of a typical sclera. However, silicone remains flexible enough to accommodate implantation and to adapt to variations in the curvature of an individual sclera. The secondary inductive coil 16 and molded body 18 are preferably oval shaped. A strap can better support an oval shaped coil.

It should be noted that the entire implant is attached to and supported by the sclera. An eye moves constantly. The eye moves to scan a scene and also has a jitter motion to improve acuity. Even though such motion is useless in the blind, it often continues long after a person has lost their sight. It is an advantage of the present design, that the entire implanted portion of the prosthesis is attached to and supported by the sclera. By placing the device under the rectus muscles with the electronics package in an area of fatty issue between the rectus muscles, eye motion does not cause any flexing which might fatigue, and eventually damage, the device.

As we improve the resolution of retinal prostheses, the number of electrodes increases. As the number of electrodes increases the number of wires between the electronics package and the electrode array must increase. This increase requires a wider thin film cable piercing the sclera. If the thin film cable is too wide, the sclerotomy may not heal properly. FIG. 2-5 present embodiments to provide for a narrower thin film cable between the electronics, external to the sclera, and the electrode array within the sclera.

A common method of reducing the conductor count in cables, is the use of a multiplexer and demultiplexer. However, multiplexers, like any electronic circuit, present unique problems when implanted within the human body. All electronics must be sealed to prevent the saline body fluids from harming the electronics and to prevent the electronics from harming the body. Each electrical wire entering and exiting the electronics package must also be sealed. Therefore it is advantageous the limit the number of such wire electronics package interconnects. While it is easy to include a multiplexer within the electronics package, it is more difficult to house a demultiplexer within the sclera.

Figure 2:
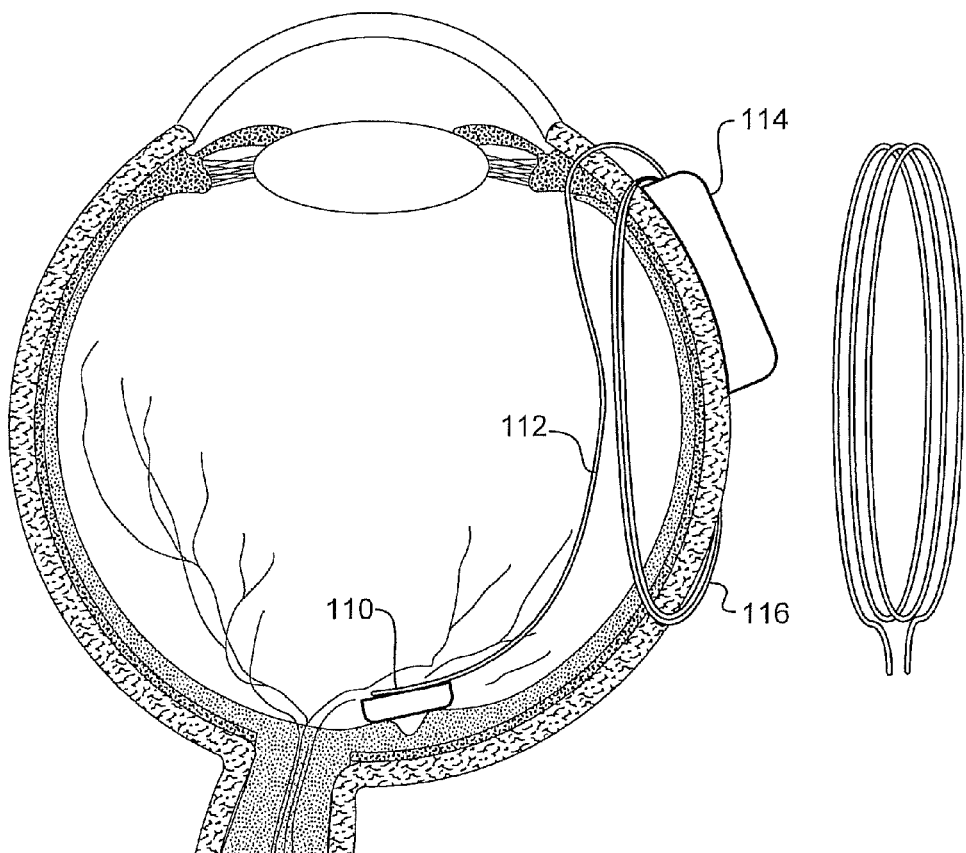
FIG. 2 depicts a retinal prosthesis with a secondary processing chip, including a demultiplexer, in the retina.

FIG. 2, depicts the preferred embodiment where a computer chip 110, including a demultiplexer is placed directly on the retina. The demultiplexer interconnects with the thin film cable 112 on one side and includes electrode openings, for contacting the retina on the other side. This is best accomplished by create feedthroughs in the silicon chip to allows electrodes on one side of the chip and connection to the flexible cable on the other side of the chip (described in more detail in FIG. 7. Cable 112 pierces the sclera and attaches to an electronics package 114. The electronics package connects to a coil 116. The chip 110 must be coated with a thin film hermetic coating as described above. This is the simplest most cost effective method of providing a demultiplexer within the sclera.

Silicon chips such as chip 110 are necessarily flat. It is possible through polishing to slightly curve one side, but the curvature is limited as the electrical circuit on the chip must be flat. It is possible that chip 110 may be a series of silicon chips bonded to a flexible membrane to approximate the curvature of the retina. This allows for a larger electrode array than would be possible with a single chip 110.

However, the retina is extremely delicate and can be damaged by either the weight of such a demultiplexer chip or chips, or by the heat generated by the demultiplexer chip. If the chip can not be made light enough or cool enough to attach to the sclera, other solutions are needed.

Figure 3:
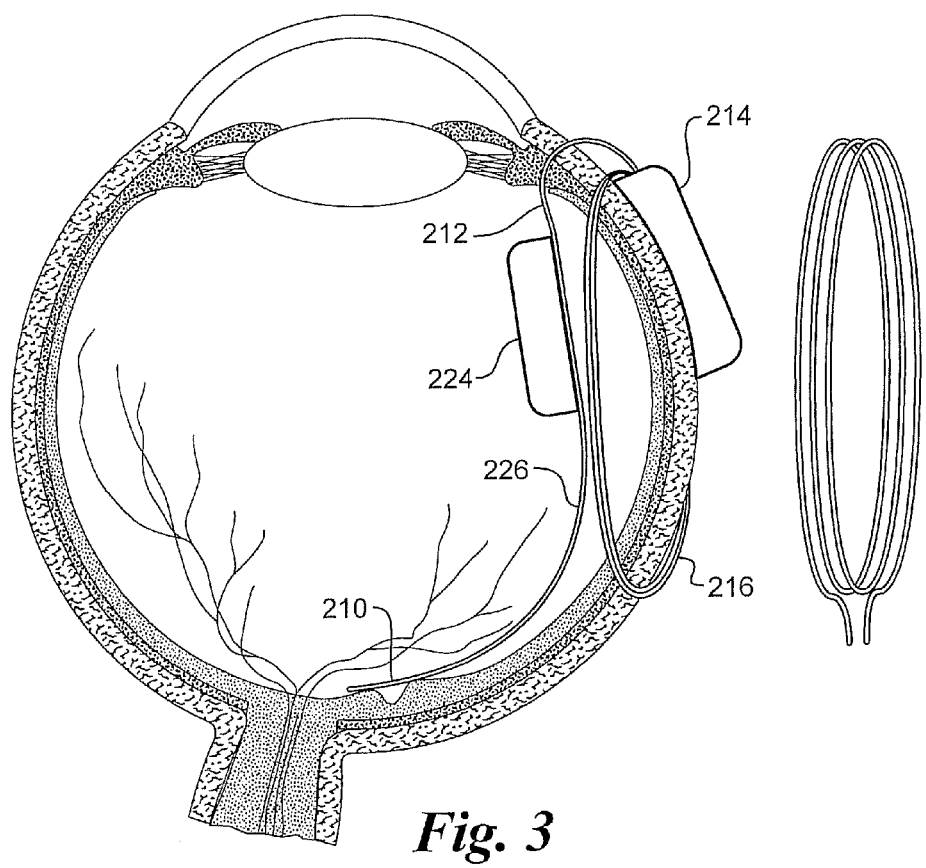
FIG. 3 depicts a retinal prosthesis with a secondary processing chip, including a demultiplexer, within the sclera but not on the retina.

FIG. 3, depicts an alternate embodiment where a demultiplexer chip 224 is positioned within the eye, but not on the retina. Electrode array 210 is connected to the demultiplexer 224 by a wide cable 226, and demultiplexer 224 is connected to the electronics package 214 by a narrow cable 212. Narrow cable 212 pierces the sclera to attach to an electronics package 214. The electronics package 214 also connects to a coil 216. This embodiment requires two interconnects on the external electronics package 214, one for the coil, and a low density interconnect to a cable piercing the sclera. This cable piercing the sclera is connected to another low density interconnect on the demultiplexer chin within the sclera. Finally there must be a high density interconnect on the demultiplexer connected to a thin film electrode array. While this solution is more complex, it moves the weight and heat of the demultiplexer off the retina.

Figure 4:
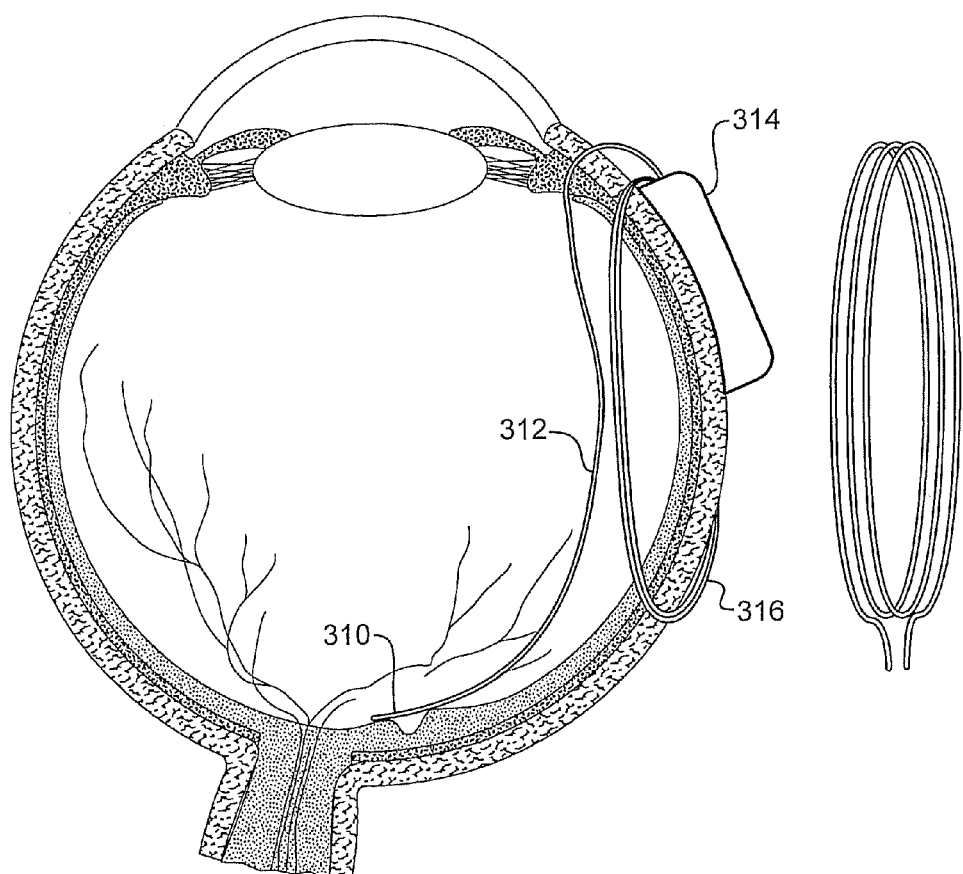
FIG. 4 depicts a retinal prosthesis with a polymer thin film based secondary processor, including a demultiplexer, on the retina.

FIG. 4, depicts yet another embodiment where the demultiplexer is not a silicon based integrated circuit, but an integrated circuit deposited directly on the thin film electrode array 310. The demultiplexer interconnects with the thin film cable 312 on one side and includes electrode openings, for contacting the retina on the other side. Cable 312 pierces the sclera and attaches to an electronics package 314. The electronics package connects to a coil 316. Several integrated circuit manufacturers are building integrated circuits on Mylar thin films. The same technique can be used to build integrated circuits on polyimide or other biocompatible thin film polymers. By depositing the demultiplexer circuitry directly on the thin film, one avoids the weight of a silicon based integrated circuit and the possible damage to the retina cause by the weight of a silicon based demultiplexer. Further, building the demultiplexer circuit directly on the thin films avoids the need for a hermetic interconnection to a demultiplexer chip or a hermetic coating on the chip. If the heat output of a thin film based demultiplexer is sufficiently small, the demultiplexer can be built directly into the electrode array, completely eliminating the need for a thin film wide enough to include one connector for each electrode.

Figure 5:
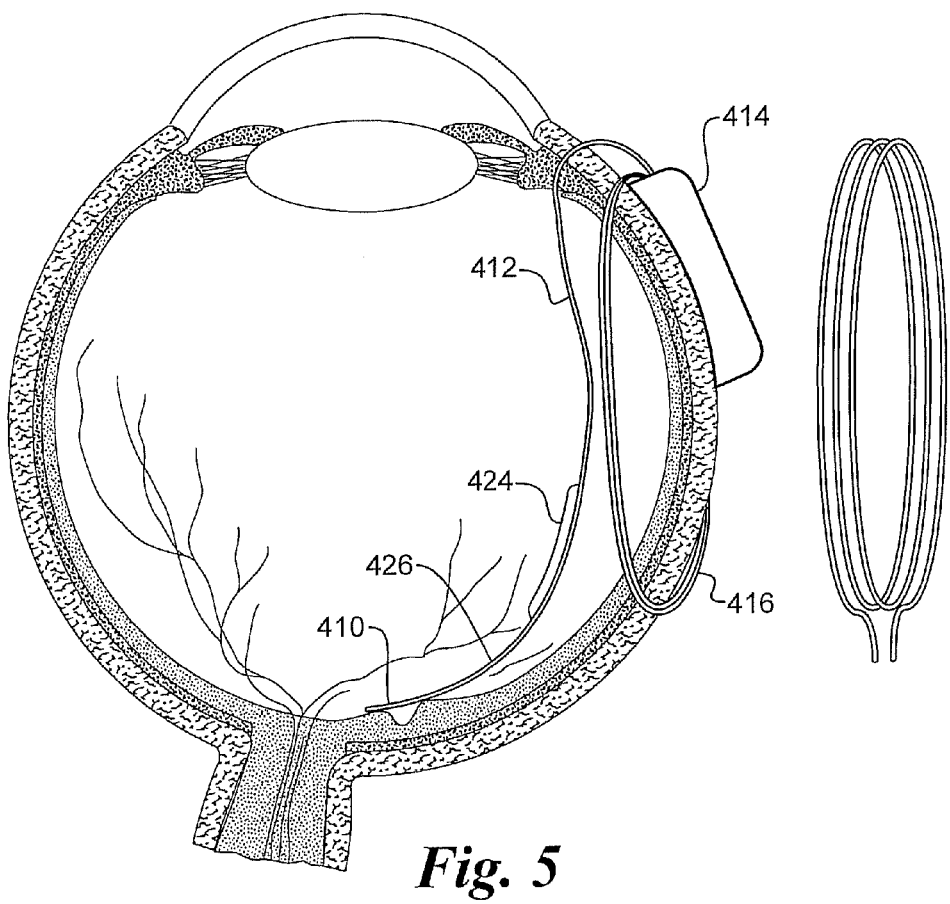
FIG. 5 depicts a retinal prosthesis with a polymer thin film based secondary processor, including a demultiplexer, within the sclera, but not on the retina.

If the heat output of a thin film demultiplexer is likely to cause damage to the retina, another embodiment, shown in FIG. 5, provides a thin film demultiplexer between the electrode array and electronics package, but sufficiently distant from the retina, to avoid heat damage. FIG. 5, depicts an alternate embodiment where a thin film demultiplexer 424 is positioned within the eye, but not on the retina. Electrode array 410 is connected to the demultiplexer 424 by a wide cable 426, and demultiplexer 424 is connected to the electronics package 414 by a narrow cable 412. Narrow cable 412 pierces the sclera to attach to an electronic package 414. The electronics package 414 connects to a coil 416. It is possible to form the electrode 410, wide cable, 426, demultiplexer 424, and thin cable 412 on a single thin film substrate. While this solution is more complex, it moves the heat of the demultiplexer off the retina.

Figure 6:
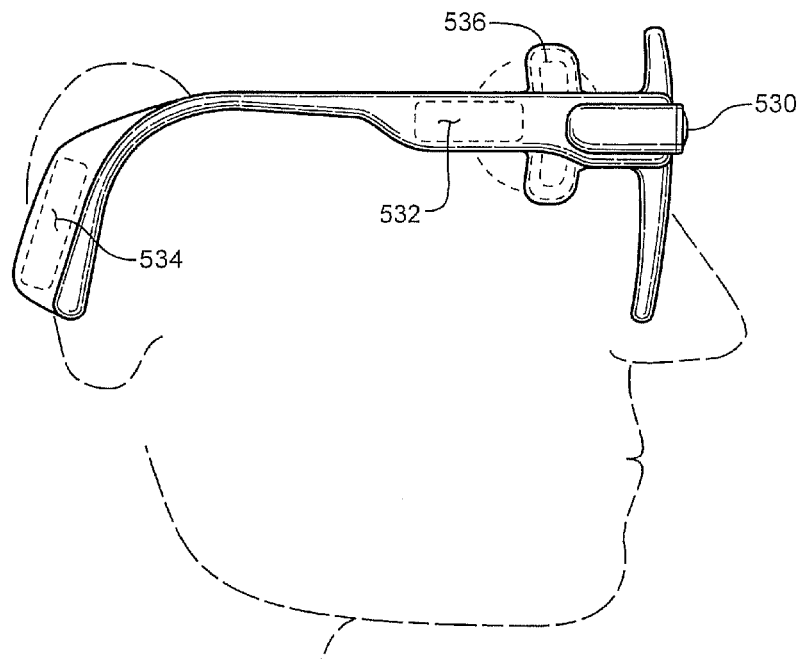
FIG. 6 is an external profile view of a user wearing the external portion of the retinal prosthesis.

FIG. 6 depicts the profile of a user wearing the external portion of the retinal prosthesis. The entire device may be built into the temple of a pair of glasses. A camera 530 collects a video image and transmits data to an external electronics package 532. A battery 534 powers the camera 530, external electronics package 532, and provides power to a primary inductive coil 536. The primary inductive coil 536 sends power and data through the skin and skull to the secondary inductive coil 16. Maximum efficiency is obtained when the primary inductive coil 536 and secondary inductive coil 16 are the same size, shape and as close together as possible.

Figure 7:
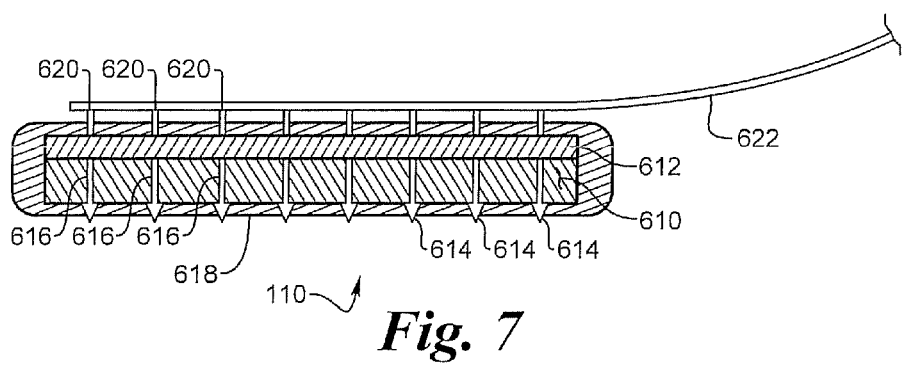
FIG. 7 is a description of the preferred demultiplexer and electrode chip.

FIG. 7, depicts the preferred demultiplexer chip 110. A silicon substrate 610 has a demultiplexer 612 applied by conventional means. Micromachining techniques are used to create voids in the silicon substrate 610, which are filled with conductive feedthroughs 616. Electrodes 614, for contact with the retina, are applied to the conductive feedthroughs 616 by electroplating or other means. A thin film hermetic coating 618 is applied to the silicon substrate 610 allowing voids for electrodes 614 and contacts 620. Finally a thin film cable 622 is attached to the contacts 620 to supply power and signal to the demultiplexer chip.

Accordingly, what has been shown is an improved retinal prosthesis. While the invention has been described by means of specific embodiments and applications thereof, it is understood that numerous modifications and variations could be made thereto by those skilled in the art without departing from the spirit and scope of the invention. It is therefore to be understood that within the scope of the claims, the invention may be practiced otherwise than as specifically described herein.

The invention claimed is:

1. A retinal prosthesis comprising:
an electrode array and integral demultiplexer suitable to be mounted internal to a sclera and in close proximity to a retina;

an electronics package encasing electronics suitable to be outside the eye;
a cable suitable to pierce the sclera electrically coupling said electrode array to said electronics package; and
a coil electrically coupled to said electronics.

2. The retinal prosthesis according to claim 1, wherein said electrode array and said demultiplexer are formed on a common substrate.

3. The retinal prosthesis according to claim 1, wherein said demultiplexer is deposited on a thin film substrate.

4. The retinal prosthesis according to claim 3, wherein said electrode array and said demultiplexer are deposited on a common thin film substrate.

5. The retinal prosthesis according to claim 4, wherein said electrode array, said demultiplexer, and said cable are deposited on a common thin film substrate.

6. The retinal prosthesis according to claim 1, further comprising:
a camera for collecting a video image;
a video processor coupled to said camera for processing said video image; and
a primary coil coupled to said video processor for transmitting said video image into a body and to said coil.

7. The retinal prosthesis according to claim 6, wherein the coil is approximately the same shape and size as the primarily coil.

8. The retinal prosthesis according to claim 1, wherein the coil is aligned with a lateral side of the sclera.

\* \* \* \* \*